(12) United States Patent
Ron Edoute et al.

(10) Patent No.: US 10,765,882 B2
(45) Date of Patent: Sep. 8, 2020

(54) SELF OPERATED ESTHETIC DEVICE WITH A SUBSTRATE

(75) Inventors: Orit Ron Edoute, Tel Aviv (IL); Oded Ron Edoute, Tel Aviv (IL)

(73) Assignee: MADRYN HEATLH PARTNERS, LP, New York, NY (US)

( * ) Notice: Subject to any disclaimer, the term of this patent is extended or adjusted under 35 U.S.C. 154(b) by 292 days.

(21) Appl. No.: 13/820,573

(22) PCT Filed: Sep. 5, 2011

(86) PCT No.: PCT/IL2011/000707
§ 371 (c)(1),
(2), (4) Date: Mar. 4, 2013

(87) PCT Pub. No.: WO2012/029065
PCT Pub. Date: Mar. 8, 2012

(65) Prior Publication Data
US 2013/0158634 A1 Jun. 20, 2013

Related U.S. Application Data

(60) Provisional application No. 61/380,231, filed on Sep. 5, 2010.

(51) Int. Cl.
*A61B 18/12* (2006.01)
*A61N 5/00* (2006.01)
(Continued)

(52) U.S. Cl.
CPC ............... *A61N 5/00* (2013.01); *A61B 18/12* (2013.01); *A61N 1/328* (2013.01); *A61N 1/40* (2013.01);
(Continued)

(58) Field of Classification Search
CPC ............ A61N 1/328; A61N 2005/0645; A61N 2007/0034; A61N 5/0625;
(Continued)

(56) References Cited

U.S. PATENT DOCUMENTS 4,243,052 A 1/1981 Bailey
6,045,575 A 4/2000 Rosen et al.
(Continued)

FOREIGN PATENT DOCUMENTS

WO 2012/029065 A2 3/2012

OTHER PUBLICATIONS

Zelickson B.D. et al., "Histological and Ultrastructural Evaluation of the Effects of a Radiofrequency-Based Nonablative Dermal Remodeling Device: A Pilot Study", Arch Dermatol, vol. 140, pp. 204-209, American Medical Association (Feb. 2004), available on-line at www.archdermatol.com.
(Continued)

*Primary Examiner* — Daniel W Fowler

(57) ABSTRACT

The present invention provides a self-operated device for treating a skin of a patient, comprising: a. a substrate having a first side and a second side; b. a plurality of RF electrodes arranged in said substrate, said RF electrodes are configured to emit RF radiation from said first side to the surface of said skin; c. at least one RF generator configured to generate pulses of current to said RF electrodes; and, d. a control unit connected to said at least one RF generator, said control unit is adapted to control the operation of said RF electrodes; wherein said control unit is adapted to control the operation of said RF electrodes according to a predetermined treatment protocol, such that the same activates or deactivates at least one of said RF electrodes at any predetermined time interval according to a predetermined pattern so as to achieve a particular therapeutic result.

31 Claims, 4 Drawing Sheets

(51) Int. Cl.
*A61N 1/32* (2006.01)
*A61N 1/40* (2006.01)
*A61B 18/00* (2006.01)
*A61N 5/06* (2006.01)
*A61N 7/00* (2006.01)
*A61B 90/00* (2016.01)

(52) U.S. Cl.
CPC ............ *A61B 2018/00452* (2013.01); *A61B 2018/00648* (2013.01); *A61B 2018/00696* (2013.01); *A61B 2018/00702* (2013.01); *A61B 2018/00714* (2013.01); *A61B 2018/00732* (2013.01); *A61B 2018/00779* (2013.01); *A61B 2018/00791* (2013.01); *A61B 2018/00845* (2013.01); *A61B 2018/00875* (2013.01); *A61B 2090/065* (2016.02); *A61N 5/0625* (2013.01); *A61N 2005/007* (2013.01); *A61N 2005/0628* (2013.01); *A61N 2005/0645* (2013.01); *A61N 2007/0034* (2013.01)

(58) Field of Classification Search
CPC .......... A61B 2018/00648; A61B 2018/00702; A61B 2018/00714; A61B 2018/00732; A61B 2018/00779; A61B 2018/00791; A61B 2018/00845; A61B 2018/00875
See application file for complete search history.

(56) References Cited

U.S. PATENT DOCUMENTS

| | | | |
|---|---|---|---|
| 6,096,066 A | 8/2000 | Chen et al. | |
| 6,139,569 A * | 10/2000 | Ingle et al. | 607/104 |
| 6,241,753 B1 | 6/2001 | Knowlton | |
| 6,290,713 B1 | 9/2001 | Russell | |
| 6,293,944 B1 | 9/2001 | Ellman et al. | |
| 6,302,874 B1 * | 10/2001 | Zhang et al. | 604/522 |
| 6,443,883 B1 | 9/2002 | Ostrow et al. | |
| 6,770,070 B1 * | 8/2004 | Balbierz | A61B 10/04 600/566 |
| 7,128,442 B2 | 10/2006 | Lee et al. | |
| 7,238,183 B2 | 7/2007 | Kreindel | |
| 7,463,927 B1 | 12/2008 | Chaouat | |
| 2003/0199862 A1 * | 10/2003 | Simpson et al. | 606/34 |
| 2004/0030227 A1 | 2/2004 | Littrup et al. | |
| 2004/0078036 A1 * | 4/2004 | Keidar | A61B 18/1492 606/41 |
| 2004/0210214 A1 * | 10/2004 | Knowlton | 606/41 |
| 2005/0043726 A1 * | 2/2005 | McHale | A61B 17/22004 606/27 |
| 2006/0241576 A1 | 10/2006 | Diederich et al. | |
| 2007/0062452 A1 | 3/2007 | Pancham et al. | |
| 2007/0088413 A1 * | 4/2007 | Weber et al. | 607/99 |
| 2007/0142885 A1 | 6/2007 | Hantash et al. | |
| 2008/0009853 A1 * | 1/2008 | Martin | A61B 18/1402 606/41 |
| 2008/0097559 A1 | 4/2008 | Eggers et al. | |
| 2008/0183164 A1 * | 7/2008 | Elkins et al. | 606/21 |
| 2008/0183251 A1 * | 7/2008 | Azar et al. | 607/101 |
| 2008/0281389 A1 * | 11/2008 | Knopp et al. | 607/115 |
| 2009/0036958 A1 | 2/2009 | Mehta | |
| 2009/0105604 A1 * | 4/2009 | Bertagnoli | A61B 90/36 600/546 |
| 2010/0016850 A1 | 1/2010 | Ron Edoute et al. | |
| 2010/0211055 A1 | 8/2010 | Eckhouse et al. | |

OTHER PUBLICATIONS

International Search Report of PCT/IL2011/000707, dated Apr. 23, 2012.
Written Opinion of the International Search Authority of PCT/IL2011/000707, dated Apr. 23, 2012.
International Preliminary Report on Patentability of PCT/IL2011/000707, dated Mar. 5, 2013.

* cited by examiner

SELF OPERATED ESTHETIC DEVICE WITH A SUBSTRATE

FIELD OF THE INVENTION

This invention generally relates to an esthetic device used for various treatment procedures for cosmetic treatment and beautification.

BACKGROUND OF THE INVENTION

Improving the appearance of the skin has been the goal of many esthetic products and procedures for many years, since a tight skin, without wrinkles or cellulite, has a younger and more appealing appearance. Apart from age related changes, the skin also suffers from exposure to chemical and physical injuries, such as tobacco, cosmetics, esthetics and radiation from the sun and other sources. Those factors contribute to the decrease in collagen production, to reduced elasticity, and the appearance of wrinkles.

A few main approaches to tightening of the skin are common practice today. The surgical approach carries disadvantages related to the anesthesia, the surgical complications, and the healing process, which may cause scars. The chemical peel approach usually involves injury to the outermost layer of the skin—the epidermis—which may cause discoloration. Since collagen fibers are found in the dermis—the subcutaneous layer of the skin, and since heat was shown to contract these fibers and generate their production [Zelickson B D, Kist D, Bernstein E, Brown D B, Ksenzenko S, Burns J, Kilmer S, Mehregan D, Pope K. Histological and ultrastructural evaluation of the effects of a radiofrequency-based nonablative dermal remodeling device: a pilot study. Arch Dermatol. 2004 February; 140 (2):204-9], methods of differentially heating the dermis (deep tissue diathermy) have recently arisen.

Different techniques for skin rejuvenation are known in art in which a substrate is used with application of light sources. For example, U.S. Pat. No. 6,096,066 discloses a flexible patch provided with a plurality of light sources mounted in spaced-apart array on its undersurface and covered with an optically transparent polymer material. The light sources are energized with an electrical current supplied by a flexible polymer battery, which is preferably rechargeable.

U.S. Pat. No. 6,045,575 discloses an apparatus for treating neonatal jaundice is in the form of a garment which has semiconductor light sources affixed thereto for radiating toward the "inside" of the garment when the infant is dressed in the garment.

U.S. Pat. No. 7,128,442 discloses an illumination unit which includes a thin and substrate and flexible electrical tracks formed on the substrate. A number of solid-state light generating sources are arranged on the substrate along the electrical tracks and are electrically connected to the electrical tracks. A flexible and optically transparent encapsulant is provided to encapsulate the light generating sources on the substrate such that the illumination unit is both thin and flexible.

U.S. Pat. No. 6,290,713 discloses flexible illuminators for external phototherapy, each having at least one light generating source, preferably a plurality of light-generating sources, on a substrate. The substrate may be a circuit board, and the light-generating source may be surface mount LEDs. Structures for diffusing light emitted from the discrete light-generating sources and/or for transferring heat away from a skin contact surface are provided. The illuminators may be formed so as to be wrapped around an infant or a limb of an adult, or may be provided in larger configurations, such as a mat. The illuminators may be passively or actively cooled so that the skin contact surface remains below a desired temperature.

Other patents disclose different treatments for increasing skin rejuvenation by RF electrodes. For example, U.S. Pat. No. 7,238,183 discloses a system and a method for treating a skin target. A temperature effector creates a temperature difference between the target and the skin tissue surrounding the target such that the target is at a higher temperature than the surrounding tissue by at least 5° C. One or more RF electrodes are attached to the skin and RF energy is applied.

U.S. Pat. No. 6,241,753 discloses a method for forming and contracting scar collagen below a tissue surface in a selected tissue site. An electromagnetic energy apparatus is provided and includes an electromagnetic energy source and a delivery device. The delivery device is positioned on the tissue surface. Electromagnetic energy is produced from the electromagnetic energy source and delivered through the tissue surface to the selected tissue site for a sufficient time to induce scar collagen formation in the selected tissue site. No more than a second degree burn is formed on the tissue surface. The scar collagen is then contracted. This method is particularly useful in tissue sites that are devoid or deficient in collagen.

One of the advantages of using RF energy for skin beautification procedures is the high energy which can be supplied to the treatment area. This high energy provides substantial treatment results which are much better, quicker and efficient than the results of which could be achieved by a light source (e.g., LEDs).

None of the prior art documents discloses a substrate which includes RF electrodes which is able to exploit the advantages of the RF electrodes with the advantages of the substrate. Therefore, there is a long felt need to develop a substrate with RF sources which will be able to provide a treatment for skin beautification.

SUMMARY OF THE INVENTION

It is one object of the present invention to provide a self-operated device for treating a skin of a patient. The device comprises:
a. a substrate having a first side and a second side;
b. a plurality of RF electrodes arranged in the substrate, the RF electrodes are configured to emit RF radiation from the first side to the surface of the skin;
c. at least one RF generator configured to generate pulses of current to the RF electrodes; and,
d. a control unit connected to the at least one RF generator, the control unit is adapted to control the operation of the RF electrodes;

It is within the scope of the present invention that the control unit is adapted to control the operation of the RF electrodes according to a predetermined treatment protocol, such that the same activates at least one of the RF electrodes at any predetermined time interval according to a predetermined pattern so as to achieve a particular therapeutic result.

It is another object of the present invention to provide the device as defined above, wherein the substrate is substantially flexible.

It is another object of the present invention to provide the device as defined above, wherein the substance is substantially soft.

It is another object of the present invention to provide the device as defined above, wherein the substance is substantially rigid.

It is another object of the present invention to provide the device as defined above, wherein the substrate is adapted to be incorporated within on object selected from the group consisting of: a bed, a mattress, a chair, any treatment apparatus, a clothing element, a garment and any combination thereof.

It is another object of the present invention to provide the device as defined above, wherein the treatment protocol is adapted to activate at any of the time intervals a substantially different set of RF electrodes; wherein the set of electrodes comprises n RF electrodes, where n equals to or greater than 1.

It is another object of the present invention to provide the device as defined above, wherein the predetermined pattern is adapted to mimic a treatment in which an applicator with RF electrodes that is moved on the surface of the skin.

It is another object of the present invention to provide the device as defined above, further comprising temperature estimation mechanism for direct or indirect measurement of the skin heat distribution and temperature.

It is another object of the present invention to provide the device as defined above, wherein the temperature estimation mechanism comprises at least one sensor selected from the group consisting of: an impedance meter for measuring impedance across the RF electrodes; thermal sensor; thermometer; light sensor, ultrasonic sensor, piezoelectric sensor, magnetic sensor, mechanical sensor, pressure sensor, and any combination thereof.

It is another object of the present invention to provide the device as defined above, wherein the device is modular.

It is another object of the present invention to provide the device as defined above, wherein the modularity of the device is provided by ability to change the size of the substrate by adding and removing elements, such that a predetermined size of the substance is received.

It is another object of the present invention to provide the device as defined above, wherein the device is a self-operable device which does not require an operator to be operated.

It is another object of the present invention to provide the device as defined above, further comprising a plurality of contact sensors in communication with the control unit, the sensors are adapted to detect the areas on the substrate in which the substrate is proximal to the skin.

It is another object of the present invention to provide the device as defined above, wherein the plurality of contact sensors are selected from the group consisting of: thermal sensors, light sensors, ultrasonic sensors, piezoelectric sensors, magnetic sensors, mechanical sensors, pressure sensors, and any combination thereof.

It is another object of the present invention to provide the device as defined above, wherein the control unit is adapted to activate or deactivate only RF electrodes in which the contact sensors detected proximity between the substrate and the skin.

It is another object of the present invention to provide the device as defined above, wherein the contact sensors are integrated with the RF electrodes.

It is another object of the present invention to provide the device as defined above, wherein the contact sensors are positioned between the RF electrodes.

It is another object of the present invention to provide the device as defined above, wherein the treatment is a safe treatment, such that unexpected thermal injury to the skin is prevented.

It is another object of the present invention to provide the device as defined above, wherein the temperate of the skin during the treatment is prevented from increasing beyond 45°.

It is another object of the present invention to provide the device as defined above, wherein the device is adapted to operate according to IEC selected from a group consisting of: IEC 60601-2-35, IEC 60601-2-2, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide the device as defined above, further comprising a feedback mechanism connected to the control unit and adapted to change the parameters of the treatment protocol, according to predetermined parameters.

It is another object of the present invention to provide the device as defined above, further comprising a feedback mechanism connected to the control unit and adapted to real-time, during treatment, alternate the parameters of the treatment protocol, according to predetermined medical need.

It is another object of the present invention to provide the device as defined above, wherein, the feedback mechanism adapted to change the current to the RF electrodes according to predetermined medical needs, the feedback mechanism comprising:

a. sensing means; adapted to sense electrotherapy parameters selected from a group consisting of dermal tensile forces, tissue impedance, muscle contraction forces, skin elasticity, a combination thereof, and any other parameter implying the treatment;

b. processing means, adopted to score analyzed tissue parameters according to a predetermined scale of treatment success; the parameters are selected from a group consisting of: dermal tensile forces, tissue impedance, muscle contraction forces, skin elasticity, a combination thereof, and any other parameter implying the treatment; and, c. regulating means, adapted to allow the treatment if the score is higher than a predetermined value and to stop the treatment if the score is lower than a predetermined value.

It is another object of the present invention to provide the device as defined above, wherein the regulating means is adapted to provide the treatment only in the surrounding of the area in which the score is higher than a predetermined value.

It is another object of the present invention to provide the device as defined above, wherein the treatment protocol comprises parameters selected from the group consisting of: power of each of the RF electrodes, length of pulse of each of the RF electrodes, frequency of each of the RF electrodes, the frequency of pulses of each of the RF electrodes, the structure of the pulses of each of the RF electrodes, the shape of the pulses of each of the RF electrodes, and any combination thereof.

It is another object of the present invention to provide the device as defined above, wherein the shape is selected from a group consisting of: triangular, rectangular, ramp, sinusoidal, composite, sawtooth shape, and any combination thereof.

It is another object of the present invention to provide the device as defined above, wherein the frequency of each of the RF electrodes ranges between about 1 Hz to about 100 MHz.

It is another object of the present invention to provide the device as defined above, wherein the length of pulse of each of the RF electrodes ranges between about 1 micro seconds to about 1000 milliseconds.

It is another object of the present invention to provide the device as defined above, wherein the parameters of the treatment protocol are changeable during the treatment according to various circumstances.

It is another object of the present invention to provide the device as defined above, wherein the various circumstances are selected from: an overheating of the skin, a preprogrammed change as part of the treatment protocol, an unexpected event, or any combination thereof.

It is another object of the present invention to provide the device as defined above, further comprising an input subsystem for manually determining the parameters of the treatment protocol.

It is another object of the present invention to provide the device as defined above, wherein the input subsystem is controllable by a person selected from the group consisting of: the patient himself, the operator, and any combination thereof.

It is another object of the present invention to provide the device as defined above, wherein the input subsystem is adapted to provide fine tuning of the parameters of the treatment protocol.

It is another object of the present invention to provide the device as defined above, wherein the fine-tuning is adapted to change the temperature generated by the RF electrodes in a range of ±2°.

It is another object of the present invention to provide the device as defined above, wherein the RF electrodes are arranged in the substrate according to a geometrical shape selected from the group consisting of: matrix shape, line, at least one circle, zig-zag, polygonal shape, irregular shape, arbitrary shape, and any combination thereof.

It is another object of the present invention to provide the device as defined above, wherein the substrate is a thin substrate which is characterized by a thickness of between about 20 micrometer to about 25 cm.

It is another object of the present invention to provide the device as defined above, wherein the substrate is made of a non-conductive but thermally conductive material.

It is another object of the present invention to provide the device as defined above, wherein the substrate is made of an electrically insulating material.

It is another object of the present invention to provide the device as defined above, wherein the substrate is made of a material selected from the group consisting of: polyimide, polyester, silicone, plastic, polymeric fabric, polyurethane, textile, cloth, of wool, flax, cotton and any combination thereof.

It is another object of the present invention to provide the device as defined above, further comprising a cooling unit adapted to cool the skin.

It is another object of the present invention to provide the device as defined above, wherein the device further comprises electronic components arranged in the substrate, the electronic components are selected from the group consisting of: resistors, capacitors, transistors, current regulators, and any combination thereof.

It is another object of the present invention to provide the device as defined above, wherein the substrate is adapted to conform to a non-planar treatment surface of the skin.

It is another object of the present invention to provide the device as defined above, wherein the substrate is adapted to be worn on the patient.

It is another object of the present invention to provide the device as defined above, further comprising an adhesive being adapted to secure the substrate from the first side to a portion of the skin, with the subtract conforming thereto.

It is another object of the present invention to provide the device as defined above, wherein the RF electrodes are adapted to heat a plurality of predetermined locations on the skin.

It is another object of the present invention to provide the device as defined above, further comprising a pulsed electromagnetic field (PEMF) frequency generator for constantly providing electromagnetic pulses to the skin of the patient.

It is another object of the present invention to provide the device as defined above, wherein the device is adapted for simultaneously applying heat by the RF electrodes and PEMF to the skin of the patient; further wherein the simultaneous application of increases the results of the treatment such that this increase is greater than the sum of the increases when the treatment is performed by the RF electrodes and the PEMF not simultaneously.

It is another object of the present invention to provide the device as defined above, wherein the electromagnetic pulse is square shaped at a frequency of 15 Hz, duration of about 5 milliseconds and intensity of 15 Gauss.

It is another object of the present invention to provide the device as defined above, wherein the shape of the electromagnetic pulse is selected from a group consisting of square wave, a sine wave, a triangular wave, sawtooth wave, ramp waves, spiked wave or any other mathematical combination.

It is another object of the present invention to provide the device as defined above, wherein the treatment is selected from the group consisting of: skin rejuvenation, smoothing wrinkles, treatment of cellulite, skin tightening circumferential reduction and any combination thereof.

It is another object of the present invention to provide the device as defined above, wherein said plurality of RF electrodes comprises N pairs of RF electrodes, each of said pairs in independent communication with RF generating means, said RF electrodes configured to transmit RF energy to said skin; further wherein said RF generator is adapted to generate N independent RF signals of predetermined waveforms, frequencies, amplitudes, and relative phases.

It is another object of the present invention to provide the device as defined above, additionally comprising control means for controlling the output of said RF generator, said control means in communication with said RF generator; and, an electrically insulating casing adapted to hold said RF electrodes such that said RF electrodes may be placed in simultaneous physical contact with said skin; wherein said N independent RF signals are phase shifted relative to one another.

It is another object of the present invention to provide the device as defined above, wherein the time-dependent amplitude $A_{t,m}$ of the mth of said N independent RF signals is given by the relationship $A_{t,m} = A_{0,m} \cdot F_m (\omega_m t + \varphi_m)$, wherein $A_{0,m}$ is a predetermined constant which greater than or equals to 1, $F_m$ is a predetermined periodic function of time, $\omega_m$ is the angular frequency of the mth RF signal, and $\varphi_m$ is a predetermined phase shift of the mth RF signal.

It is another object of the present invention to provide the device as defined above, wherein for each of said N independent RF signals, $$\varphi_m = \frac{\pi(m-1)k}{N},$$

where $0 \le k \le 1$ and $m = 1, 2, 3 \ldots N$; where N is the amount of said RF electrodes pairs.

It is another object of the present invention to provide the device as defined above, wherein $F_m$ is chosen from the group consisting of sine, cosine, tan, cotangents (cot), sawtooth wave, triangular wave, square wave, rectangular wave, trapezoidal wave, and any combination of the above.

It is another object of the present invention to provide the device as defined above, wherein each of said predetermined frequencies is between about 1 Hz and about 100 MHz.

It is another object of the present invention to provide the device as defined above, wherein said RF signals are transmitted in either a continues mode or in pulses.

It is another object of the present invention to provide the device as defined above, wherein, when the RF is applied in pulses, the length of said pulses is between about 0.01 micro-sec and about 1 ms.

It is another object of the present invention to provide the device as defined above, additionally comprising means adapted to apply Pulsed Electromagnetic Field Therapy (PEMF).

It is another object of the present invention to provide the device as defined above, wherein the length of said pulses is between about 0.1 and about 1000 ms.

It is another object of the present invention to provide the device as defined above, further comprising temperature measuring means adapted to measure the temperature of the surface of said skin.

It is another object of the present invention to provide the device as defined above, wherein said temperature measuring means comprises at least one sensor chosen from the group consisting of impedance meter adapted to measure impedance across at least one of said pairs of RF electrodes; thermal sensor; thermometer; and any combination thereof.

It is another object of the present invention to provide the device as defined above, wherein said temperature measuring means are either come into contact with the skin or not in contact with the skin.

It is another object of the present invention to provide the device as defined above, wherein said control means are programmed to regulate the amount of RF energy transmitted to said skin such that the temperature of said skin remains within a predetermined range.

It is another object of the present invention to provide the device as defined above, wherein said predetermined range is between ambient temperature and 50° C.

It is another object of the present invention to provide the device as defined above, wherein said predetermined range is between 30° C. and 100° C.

It is another object of the present invention to provide the device as defined above, wherein said electrodes are disposed about the distal end of said casing in a geometry chosen from the group consisting of linear; zigzag; on the perimeter of a shape chosen from substantially polygonal, circular, oval, or irregular; within the area of a shape chosen from substantially polygonal, circular, oval, or irregular; and any combination of the above.

It is another object of the present invention to provide the device as defined above, wherein the power transmitted by said RF electrodes and said RF generating means to said skin is between 1 W and 700 W.

It is another object of the present invention to provide the device as defined above, wherein said cosmetic improvement is chosen from the group consisting of skin rejuvenation, reduction of the number of wrinkles, reduction of the depth of wrinkles, reduction of cellulite, skin tightening, circumferential reduction, and any combination of the above.

It is another object of the present invention to provide the device as defined above, further comprising cooling means adapted to cool said skin.

It is another object of the present invention to provide the device as defined above, wherein said cooling means are chosen from the group consisting of a Peltier effect cooling device, irrigation with cool water, and means for blowing air across the skin.

It is another object of the present invention to provide the device as defined above, wherein said RF electrodes are further adapted to provide heat to said skin.

It is another object of the present invention to provide the device as defined above, further comprising a deep tissue diathermy device.

It is another object of the present invention to provide the device as defined above, wherein said deep tissue diathermy device is chosen from the group consisting of any devices emitting RF radiation and any other means adapted for producing electrical current absorbed by subcutaneous tissue.

It is another object of the present invention to provide the device as defined above, wherein said deep tissue diathermy device further comprises:
  i. at least one electrical output device adapted to generate RF electromagnetic energy; and,
  ii. at least two electrodes electrically coupled to said electrical output device and placed on said skin region, wherein all said electrodes are adapted to simultaneously apply said RF energy to said skin.

It is another object of the present invention to provide the device as defined above, wherein said deep tissue diathermy device further comprises:
  i. at least one electrical output device adapted to generate electrical current; and,
  ii. at least two electrodes electrically coupled to said electrical output device and placed on said skin region, wherein all of said electrodes are adapted to simultaneously apply said electrical current to said skin.

It is another object of the present invention to provide the device as defined above, wherein said deep tissue diathermy device is chosen from the group consisting of acoustic (e.g., ultrasonic) diathermy devices, optical diathermy devices, electromagnetic induction diathermy devices, devices for producing sound waves, ultrasonic diathermy devices, and devices for direct application of heat.

It is another object of the present invention to provide the device as defined above, wherein said deep tissue diathermy device is an optical device adapted to emit light in wavelengths absorbed by subcutaneous tissue such that said subcutaneous tissue is heated.

It is another object of the present invention to provide the device as defined above, wherein said deep tissue diathermy device is a device for producing sound waves adapted to emit sound waves of a frequency absorbed by the subcutaneous tissue such that said subcutaneous tissue is heated.

It is another object of the present invention to provide the device as defined above, wherein said control means are adapted to monitor physical tissue parameters and to change at least one of (a) the amount of heat applied and (b) the form of said RF in response to the values of said physical tissue parameters.

It is another object of the present invention to provide the device as defined above, wherein said control means further comprise:
i. processing means adapted to store in a communicable database predetermined parameters defining safe and unsafe treatment parameters, said parameters chosen from the group consisting of time of said treatment, the temperature of said skin, frequency, power, energy applied by said RF generating means, depth to which said device operates, magnetic field intensity, tissue impedance, specific absorption rate, superficial muscle contractions and any combination thereof;
ii. sensing means adapted to sense electromagnetic radiation and heat radiation parameters chosen from a group consisting of time of said treatment, temperature of said tissue, frequency, power, intensity of ultrasound irradiation, energy applied by said RF generating means, depth to which said device operates, magnetic field intensity, tissue impedance, specific absorption rate, superficial muscle contractions and any combination thereof; and,
iii. regulating means adapted to stop the operation of said device if said parameters are determined to be unsafe.

It is another object of the present invention to provide the device as defined above, wherein said control means additionally comprise a feedback mechanism, adapted to change said RF signal according to predetermined medical needs, and comprising:
i. sensing means adapted to monitor electrotherapy parameters related to the level of skin rejuvenation and viability;
ii. processing means, adapted to determine the degree of esthetic improvement in at least one tissue parameter related to the level of skin rejuvenation and vitality; and,
iii. regulating means adapted to stop the operation of said device when said degree of esthetic improvement reaches a predetermined value.

It is another object of the present invention to provide the device as defined above, wherein said electrotherapy parameters are chosen from the group consisting of dermal tensile forces, tissue impedance, muscle contraction forces, skin elasticity, and any combination thereof.

It is another object of the present invention to provide the device as defined above, wherein said at least one tissue parameter is chosen from the group consisting of dermal tensile forces, tissue impedance, muscle contraction forces, skin elasticity, and any combination thereof.

It is another object of the present invention to provide the device as defined above, wherein said sensing means are adapted to sense electrotherapy parameters are chosen from the group consisting of time of said treatment, temperature of said tissue, frequency, power, tissue impedance, superficial muscle contractions and any combination thereof.

It is another object of the present invention to provide the device as defined above, wherein said processing means are adapted to store in a communicable database predetermined parameters defining safe and unsafe treatment conditions.

It is another object of the present invention to provide the device as defined above, wherein said predetermined parameters are chosen from the group consisting of time of said treatment, temperature of said tissue, frequency, power, tissue impedance, superficial muscle contractions, and any combination thereof.

It is another object of the present invention to provide the device as defined above, additionally comprising means for massaging said skin.

It is another object of the present invention to provide the device as defined above, wherein at least one of said RF electrodes comprises a hypodermic syringe for penetrating into subcutaneous tissue.

It is another object of the present invention to provide the device as defined above, additionally comprising at least one acoustic transducer in communication with said substrate, adapted for producing ultrasonic waves. It is another object of the present invention to provide the device as defined above, additionally comprising at least one first coil wrapped around at least a portion of said at least one acoustic transducer.

It is another object of the present invention to provide the device as defined above, wherein said at least one acoustic transducer is a piezoelectric transducer.

It is another object of the present invention to provide the device as defined above, additionally comprising a plurality of acoustic transducers, wherein a single coil is wrapped around all of said acoustic transducers.

It is another object of the present invention to provide the device as defined above, additionally comprising means for evacuating at least a portion of the skin so as to apply either pulses of suction or a constant vacuum.

It is another object of the present invention to provide the device as defined above, further comprising temperature measurement means and control means adapted to regulate at least one said RF electrical current, said time-varying current, and said alternating current such that the measured skin temperature does not go outside of predetermined limits.

It is another object of the present invention to provide the device as defined above, wherein said predetermined limits are ambient temperature and 45° C.

It is another object of the present invention to provide the device as defined above, wherein said predetermined limits are ambient temperature and 50° C.

It is another object of the present invention to provide the device as defined above, wherein said predetermined limits are 30° C. and 100° C.

It is another object of the present invention to provide the device as defined above, further comprising means for cooling the skin.

It is another object of the present invention to provide the device as defined above, wherein said means for cooling the skin is chosen from the group consisting of a Peltier effect cooling device, irrigation with cool water, and means for blowing air.

It is another object of the present invention to provide the device as defined above, additionally comprising at least one selected from a group consisting of light means, laser means, electrical energy generating means and any combination thereof embedded within said substrate.

It is another object of the present invention to provide a method for treating a skin of a patient. The method comprises steps of
a. providing a self-operated device for treating a skin of a patient, comprising: (i) a substrate having a first side and a second side; (ii) a plurality of RF electrodes arranged in the substrate, the RF electrodes are configured to emit RF radiation from the first side to the surface of the skin; (iii) at least one RF generator configured to generate pulses of current to the RF electrodes; and, (iv) a control unit connected to the at least one RF generator, the control unit is adapted to control the operation of the RF electrodes;

b. at least partially contacting or adjacently bringing the substrate with the skin of the patient;

c. activating at least one of the RF electrodes at any predetermined time interval according to a predetermined pattern; and, d. controlling the RF electrodes according to a predetermined treatment protocol thereby achieving a particular therapeutic result.

It is another object of the present invention to provide the method as defined above, wherein the substrate is substantially flexible.

It is another object of the present invention to provide the method as defined above, wherein the substance is either substantially soft or rigid.

It is another object of the present invention to provide the method as defined above, wherein the step (b) of contacting the substrate further comprising step of locating the patient on an object selected from the group consisting of: a bed, a mattress, a chair, any treatment apparatus, a clothing element, a garment and any combination thereof.

It is another object of the present invention to provide the method as defined above, further comprising step of activating at any of the time intervals a substantially different set of RF electrodes according to the treatment protocol wherein the set of RF electrodes comprises n RF electrodes, where n equals to or greater than 1.

It is another object of the present invention to provide the method as defined above, wherein the predetermined pattern is adapted to mimic a treatment in which an applicator with RF electrodes that is moved on the surface of the skin.

It is another object of the present invention to provide the method as defined above, further comprising step of directly and indirectly measuring the heat distribution and temperature of the skin via a temperature estimation mechanism.

It is another object of the present invention to provide the method as defined above, wherein the temperature estimation mechanism comprises at least one sensor selected from the group consisting of: an impedance meter for measuring impedance across the RF electrodes; thermal sensor; thermometer; lights sensor, ultrasonic sensor, piezoelectric sensor, magnetic sensor, mechanical sensor, pressure sensor, and any combination thereof.

It is another object of the present invention to provide the method as defined above, wherein the device does not require an operator to be operated.

It is another object of the present invention to provide the method as defined above, further comprising step of detecting the areas on the substrate in which the substrate is proximal to the skin via a plurality of contact sensors in communication with the control unit.

It is another object of the present invention to provide the method as defined above, wherein the plurality of contact sensors are selected from the group consisting of: thermal sensors, light sensors, ultrasonic sensors, piezoelectric sensors, magnetic sensors, mechanical sensors, pressure sensors, and any combination thereof.

It is another object of the present invention to provide the method as defined above, wherein the control unit is adapted to activate or deactivate only RF electrodes in which the contact sensors detected proximity between the substrate and the skin.

It is another object of the present invention to provide the method as defined above, wherein the contact sensors are integrated with the RF electrodes.

It is another object of the present invention to provide the method as defined above, wherein the contact sensors are positioned between the RF electrodes.

It is another object of the present invention to provide the method as defined above, wherein the treatment is a safe treatment, such that unexpected thermal injury to the skin is prevented.

It is another object of the present invention to provide the method as defined above, further comprising step of preventing the temperate of the skin to increase beyond 45° during the treatment.

It is another object of the present invention to provide the method as defined above, wherein the device is adapted to operate according to IEC selected from a group consisting of: IEC 60601-2-35, IEC 60601-2-2, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide the method as defined above, further comprising steps of providing the device with a feedback mechanism connected to the control unit; and changing the parameters of the treatment protocol, according to predetermined parameters.

It is another object of the present invention to provide the method as defined above, further comprising step of real-time, during treatment, alternating the parameters of the treatment protocol, according to predetermined medical need.

It is another object of the present invention to provide the method as defined above, wherein the feedback mechanism adapted to change the current to the RF electrodes according to predetermined medical needs, the feedback mechanism comprising:

a. sensing means; adapted to sense electrotherapy parameters selected from a group consisting of dermal tensile forces, tissue impedance, muscle contraction forces, skin elasticity, a combination thereof, and any other parameter implying the treatment;

b. processing means, adopted to score analyzed tissue parameters according to a predetermined scale of treatment success; the parameters are selected from a group consisting of: dermal tensile forces, tissue impedance, muscle contraction forces, skin elasticity, a combination thereof, and any other parameter implying the treatment; and, c. regulating means, adapted to allow the treatment if the score is higher than a predetermined value and to stop the treatment if the score is lower than a predetermined value.

It is another object of the present invention to provide the method as defined above, wherein the regulating means is adapted provide the treatment only in the surrounding of the area in which the score is higher than a predetermined value.

It is another object of the present invention to provide the method as defined above, wherein the treatment protocol comprises parameters selected from the group consisting of: power of each of the RF electrodes, length of pulse of each of the RF electrodes, frequency of each of the RF electrodes, the frequency of pulses of each of the RF electrodes, the structure of the pulses of each of the RF electrodes, the shape of the pulses of each of the RF electrodes, and any combination thereof.

It is another object of the present invention to provide the method as defined above, wherein the shape is selected from a group consisting of: triangular, rectangular, ramp, sinusoidal, composite, sawtooth shape, and any combination thereof.

It is another object of the present invention to provide the method as defined above, wherein the frequency of each of the RF electrodes ranges between about 1 Hz to about 100 MHz.

It is another object of the present invention to provide the method as defined above, wherein the length of pulse of each of the RF electrodes ranges between about 1 micro seconds to about 1000 milliseconds.

It is another object of the present invention to provide the method as defined above, further comprising step of manually determining the parameters of the treatment protocol via an input subsystem.

It is another object of the present invention to provide the method as defined above, wherein the input subsystem is controllable by a person selected from the group consisting of: the patient himself, the operator, and any combination thereof.

It is another object of the present invention to provide the method as defined above, wherein the input subsystem is adapted to provide fine tuning of the parameters of the treatment protocol.

It is another object of the present invention to provide the method as defined above, wherein the fine-tuning is adapted to change the temperature generated by the RF electrodes in a range of ±2°.

It is another object of the present invention to provide the method as defined above, wherein the RF electrodes are arranged in the substrate according to a geometrical shape selected from the group consisting of: matrix shape, line, at least one circle, zig-zag, polygonal shape, irregular shape, arbitrary shape, and any combination thereof.

It is another object of the present invention to provide the method as defined above, further comprising step of providing the device as a modular device.

It is another object of the present invention to provide the method as defined above, wherein the modularity of the device is provided by ability to change the size of the substrate by adding and removing elements, such that a predetermined size of the substance is received.

It is another object of the present invention to provide the method as defined above, wherein the substrate is a thin substrate which is characterized by a thickness of between about 20 micrometer to about 25 cm.

It is another object of the present invention to provide the method as defined above, wherein the substrate is made of a non-conductive but thermally conductive material.

It is another object of the present invention to provide the method as defined above, wherein the substrate is made of an electrically insulating material.

It is another object of the present invention to provide the method as defined above, wherein the substrate is made of a material selected from the group consisting of: polyimide, polyester, silicone, plastic, polymeric fabric, polyurethane, textile, cloth, of wool, flax, cotton and any combination thereof.

It is another object of the present invention to provide the method as defined above, further comprising a cooling unit adapted to cool the skin.

It is another object of the present invention to provide the method as defined above, wherein the device further comprises electronic components arranged in the substrate, the electronic components are selected from the group consisting of: resistors, capacitors, transistors, current regulators, and any combination thereof.

It is another object of the present invention to provide the method as defined above, wherein the substrate is adapted to conform to a non-planar treatment surface of the skin.

It is another object of the present invention to provide the method as defined above, wherein the substrate is adapted to be worn on the patient.

It is another object of the present invention to provide the method as defined above, further comprising step of providing the device with an adhesive which is adapted to secure the substrate from the first side to a portion of the skin, with the subtract conforming thereto.

It is another object of the present invention to provide the method as defined above, wherein the RF electrodes are adapted to heat a plurality of predetermined locations on the skin.

It is another object of the present invention to provide the method as defined above, further comprising step of providing the device with a pulsed electromagnetic field (PEMF) frequency generator for constantly providing electromagnetic pulses to the skin of the patient.

It is another object of the present invention to provide the method as defined above, wherein the device is adapted for simultaneously applying heat by the RF electrodes and PEMF to the skin of the patient; further wherein the simultaneous application of increases the results of the treatment such that this increase is greater than the sum of the increases when the treatment is performed by the RF electrodes and the PEMF not simultaneously.

It is another object of the present invention to provide the method as defined above, wherein the electromagnetic pulse is square shaped at a frequency of 15 Hz, duration of about 5 milliseconds and intensity of 15 Gauss.

It is another object of the present invention to provide the method as defined above, wherein the shape of the electromagnetic pulse is selected from a group consisting of square wave, a sine wave, a triangular wave, sawtooth wave, ramp waves, spiked wave or any other mathematical combination.

It is another object of the present invention to provide the method as defined above, wherein the treatment is selected from the group consisting of: skin rejuvenation, smoothing wrinkles, treatment of cellulite, skin tightening circumferential reduction and any combination thereof.

BRIEF DESCRIPTION OF THE FIGURES

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
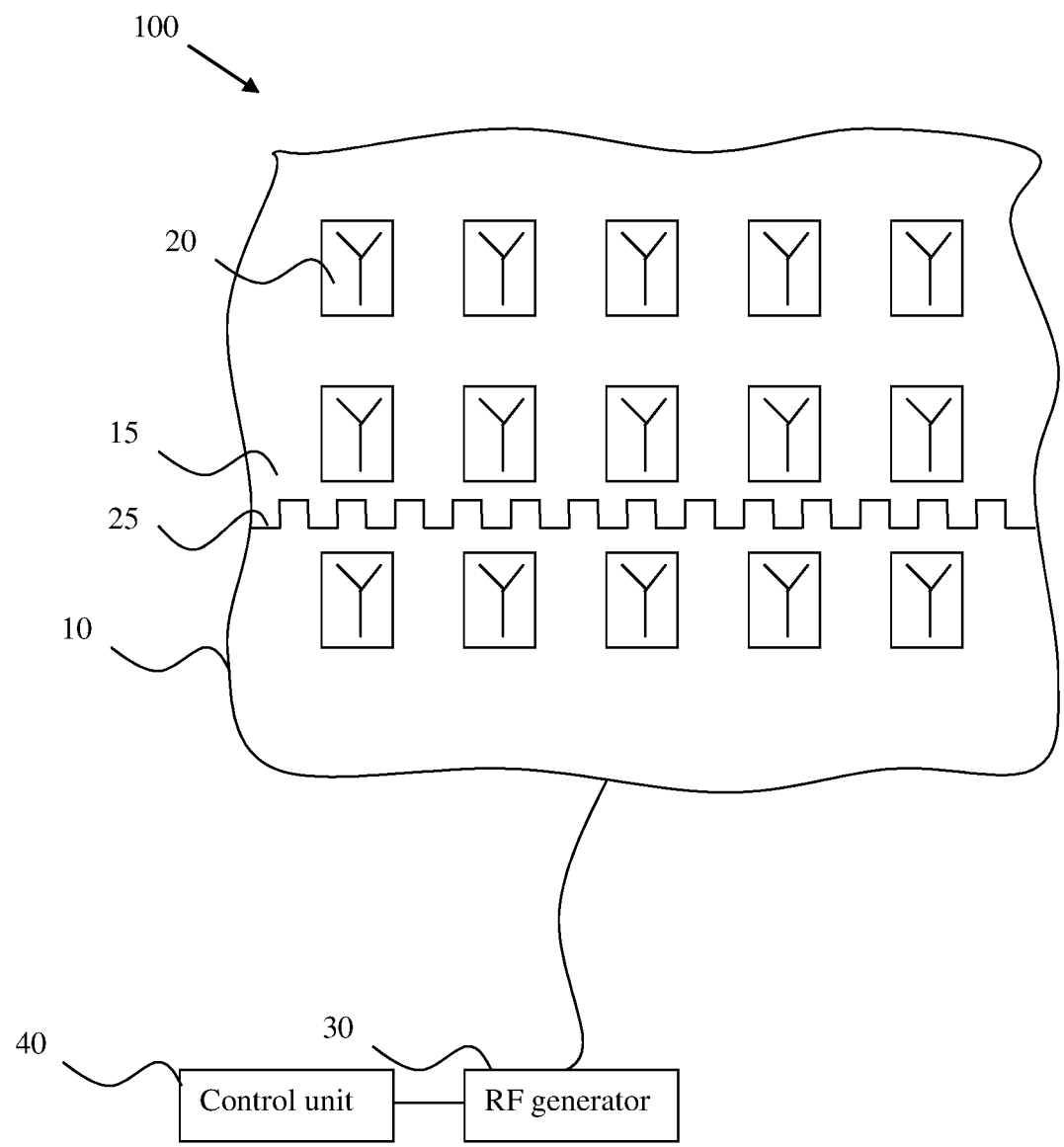
FIG. 1 is an illustration of the device of the present invention according to a specific embodiment.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The term 'substrate' refers hereinafter to any sheet (e.g., polymeric sheet) in which all the electronic components are coupled to or integrated to. The substrate may be a flexible substrate or a rigid substrate.

The term "Radio Frequency (RF)" refers hereinafter in a non-limiting manner to an electromagnetic spectrum with frequency range of about 3 Hz to about 300 GHz.

The term "collagen" refers hereinafter in a non-limiting manner to a long, fibrous structural protein which is a major component of the extracellular matrix that supports most tissues and gives cells structure. It is responsible for skin strength and elasticity, and its degradation leads to wrinkles that accompany aging.

The term "epidermis" refers hereinafter in a non-limiting manner to the outermost layer of the skin.

The term "dermis" refers hereinafter in a non-limiting manner to a layer of skin beneath the epidermis that consists of connective tissue, and cushions the body from stress and strain.

The term "safe treatment parameters" are the parameters of the device which may be selected from the group consisting of: time t of said treatment, temperature T of said tissue, duty cycle t/T, Frequency F, power P, tissue impedance, superficial muscle contractions or a combination thereof;

The term "IEC 60601-1-1" refers hereinafter to medical electrical equipment standard. More specifically it refers to general requirements for safety—Collateral standard: Safety requirements for medical electrical systems. The IEC 60601-1 set of standards are divided into three distinct areas. The first area is the basic standard IEC 60601-1. This is the general requirement for all electrical medical based products. The second area is the collateral standards, which cover across the board issues such as combining into a system with other devices, EMC, radiation protection, and programmable electronic medical systems (software, firmware, etc.). The standard numbers are IEC 60601-1-1, -1-2, -1-3, and -1-4 respectively. The third area is the particular standards that deal with a specific type of medical device. The particular standards are identified as IEC 60601-2-XX where XX identifies the particular standard number for the particular type of medical equipment. An example would be IEC 60601-2-3 which is the particular standard for short-wave therapy equipment.

The term "IEC 60601-1-2" refers hereinafter to medical electrical equipment standard. More specifically it refers to general requirements for basic safety and essential performance—Collateral standard: Electromagnetic compatibility—Requirements and tests.

The term "IEC 60601-1-4" refers hereinafter to medical electrical equipment standard. More specifically it refers to general requirements for safety—Collateral Standard: Programmable electrical medical systems.

The term "IEC 60601-1-6" refers hereinafter to medical electrical equipment standard. More specifically it refers to general requirements for basic safety and essential performance—Collateral standard: Usability.

The term "IEC 60601-1-8" refers hereinafter to medical electrical equipment standard. More specifically it refers to general requirements for basic safety and essential performance—Collateral Standard: General requirements, tests and guidance for alarm systems in medical electrical equipment and medical electrical systems.

The term "IEC 60601-2-3" refers hereinafter to medical electrical equipment standard. More specifically it refers to particular requirements for the safety of short-wave therapy equipment.

The term "IEC 60601-2-4" refers hereinafter to medical electrical equipment standard. More specifically it refers to particular requirements for the safety of cardiac defibrillators and cardiac defibrillators—monitors.

The term "IEC 60601-2-9" refers hereinafter to medical electrical equipment. More specifically it refers to particular requirements for the safety of patient contact dosemeters used in radiotherapy with electrically connected radiation detectors.

The term "IEC 60601-2-10" refers hereinafter to medical electrical equipment. More specifically it refers to particular requirements for the safety of nerve and muscle stimulators.

The term "IEC 60601-2-25" refers hereinafter to medical electrical equipment standard. More specifically it refers to particular requirements for the basic safety of electrocardiographs.

The term "IEC 60601-2-27" refers hereinafter to medical electrical equipment standard. More specifically it refers to particular requirements for the safety electrocardiographic monitoring equipment.

The term "IEC 60601-2-35" refers hereinafter to medical electrical equipment standard. More specifically it refers to particular requirements for the safety of blankets, pads and mattresses intended for heating in medical use.

The term "IEC 60601-2-40" refers hereinafter to medical electrical equipment standard. More specifically it refers to particular requirements for the safety of electromyographs and evoked response equipment.

The term "IEC 60601-2-47" refers hereinafter to medical electrical equipment standard. More specifically it refers to particular requirements for the safety, including essential performance, of ambulatory electrocardiographic systems.

The term "IEC 60601-2-49" refers hereinafter to medical electrical equipment standard. More specifically it refers to particular requirements for the safety of multifunction patient monitoring equipment.

The term "IEC 60601-2-2" refers hereinafter to Medical electrical equipment. More particularly, it refers to the basic safety and essential performance of high frequency surgical equipment and high frequency surgical accessories.

The present invention relates to a physical therapeutic device in which skin beautification (e.g., skin tightening, skin rejuvenation, cellulite treatment or any other cosmetic treatment etc.) may be achieved. According to some embodiments, the present invention provides a device and a method for applying electrical signals to a desired region of the skin and enabling to achieve a skin tightening and lifting, and even smoothening wrinkles.

The thermal effect which is used in the present invention includes heating the tissue such that when the tissue is heated to a sufficiently high temperature, tissue injury is produced. Furthermore, when heat is generated within the dermis, it usually causes contraction and thickening of collagen fibers. This results in an overall tightened and rejuvenated appearance of the skin. Heat within the dermis creates a limited thermal injury. The natural response of the body to this injury is to produce collagen at the site of the wound. This results in firmer, thicker, more youthful skin. Usually the skin is heated to temperatures in the range of about 37 degrees and about 45 degrees for short periods of time.

It is an object of the present invention to provide a safe treatment with RF energy, such that unexpected thermal injury to the skin is prevented. The damage which may occur is an expected damage which is part of the treatment produce. This is performed by efficiently controlling the operation of RF electrodes. For example, according to some embodiments, the temperature of the skin during the treatment is prevented from increasing beyond 37° and preferably bellow 45 degrees.

According to different embodiments of the present invention, the treatment may be for example for treating the following: skin rejuvenation, smoothing wrinkles, treatment of cellulite, skin tightening circumferential reduction and any combination thereof.

Reference is now made to FIG. 1 which schematically illustrates a specific embodiment of the present invention of self-operated device 100 for treating a skin of a patient (e.g., for skin rejuvenation). According to this embodiment, device 100 comprises the following components:

a. A substrate 10 which has a first side 15 and a second side (not shown).
b. A plurality of RF electrodes 20 arranged in substrate 10. RF electrodes 20 are configured to emit RF radiation from first side 15 to the surface of the skin.
c. At least one RF generator 30 configured to generate pulses of current to RF electrodes.
d. A control unit 40 connected to RF generator, the control unit is adapted to control the operation of RF electrodes 20.

According to some embodiments, substrate 10 is substantially flexible. According to other embodiments substance 10 is substantially soft. According to another embodiments substance 10 is substantially rigid.

According to some embodiments, substrate 10 is adapted to be incorporated within on object selected from the group consisting of a bed, a chair, a mattress, a treatment apparatus, and any combination thereof. In this embodiment, the patient may be located on the object, and the treatment may be provided to the patient while there is a contact between the patient and the device.

According to another embodiment, the substrate 10 is a clothing element, a garment and any combination thereof which is worn on the patient.

According to another embodiment, the substrate 10 is either flexible of rigid element.

Control unit 40 may control the operation of RF electrodes 20 according to a predetermined treatment protocol. According to some embodiments, the treatment protocol may activate RF electrodes 20 according to a predetermined pattern so as to achieve a particular therapeutic result. For example, this predetermined pattern may mimic a known in the art treatment in which an applicator with RF electrodes is manually moved on the surface of the skin.

According to some embodiments, RF electrodes 20 are arranged in the substrate according to a geometrical shape selected from the group consisting of: matrix shape, line, at least one circle, zig-zag, polygonal shape, irregular shape, arbitrary shape, and any combination thereof.

As part of its operation, device 10 may use a temperature estimation mechanism. This mechanism may estimate the skin heat distribution and temperature by a direct or indirect measurement. This may be done via at least one sensor selected from the group consisting of: an impedance meter for measuring impedance across the RF electrodes; thermal sensor; thermometer; light sensor, ultrasonic sensor, piezoelectric sensor, magnetic sensor, mechanical sensor, pressure sensor, and any combination thereof. This may also be done via other known in the art means which can estimate temperature and heat distribution.

Due to the treatment protocol, and the simplicity in the operation of device 100, in some embodiments the device may be a self-operable device which does not require an operator to be operated. According to these embodiments, the user may put substrate 10 on his skin, and active a predetermined treatment program which will provide safe treatment and efficient results.

According to certain embodiments, device 100 may comprise a plurality of contact sensors in communication with control unit 40. The contact sensors are adapted to detect the areas on the substrate in which the substrate is proximal to the skin. This detection may be used for activating RF sensors in which there is a contact with the skin, and not to active RF sensors in which there is not contact with the skin of the patient.

According to certain embodiments, the contact sensors may be integrated with the RF electrodes in a single sensor unit. According to other embodiments, the contact sensors may be positioned between the RF electrodes.

By this detection, the treatment may be more safe and efficient. According to different embodiment, the plurality of the contact sensors may be selected from the group consisting of: thermal sensors, lights sensors, ultrasonic sensors, piezoelectric sensors, magnetic sensors, mechanical sensors, pressure sensors, and any combination thereof.

According to different embodiments, control unit 40 is adapted to activate or deactivate only RF electrodes in which the sensors detected proximity between the substrate and the skin.

According to some embodiments, device 100 further comprises a feedback mechanism connected to control unit 40 and adapted to change the parameters of the treatment protocol. The feedback mechanism is adapted to change the current to the RF electrodes according to predetermined medical needs. The feedback mechanism may comprise:

a. sensing means; adapted to sense electrotherapy parameters selected from a group consisting of dermal tensile forces, tissue impedance, muscle contraction forces, skin elasticity, a combination thereof, and any other parameter implying the treatment;
b. processing means, adopted to score analyzed tissue parameters according to a predetermined scale of treatment success; the parameters are selected from a group consisting of: dermal tensile forces, tissue impedance, muscle contraction forces, skin elasticity, a combination thereof, and any other parameter implying the treatment; and,
c. regulating means, adapted to allow the treatment if the score is higher than a predetermined value and to stop the treatment if the score is lower than a predetermined value.

According to some embodiments, the regulating means is adapted to said treatment only in the surrounding of the area in which said score is higher than a predetermined value.

Figure 2:
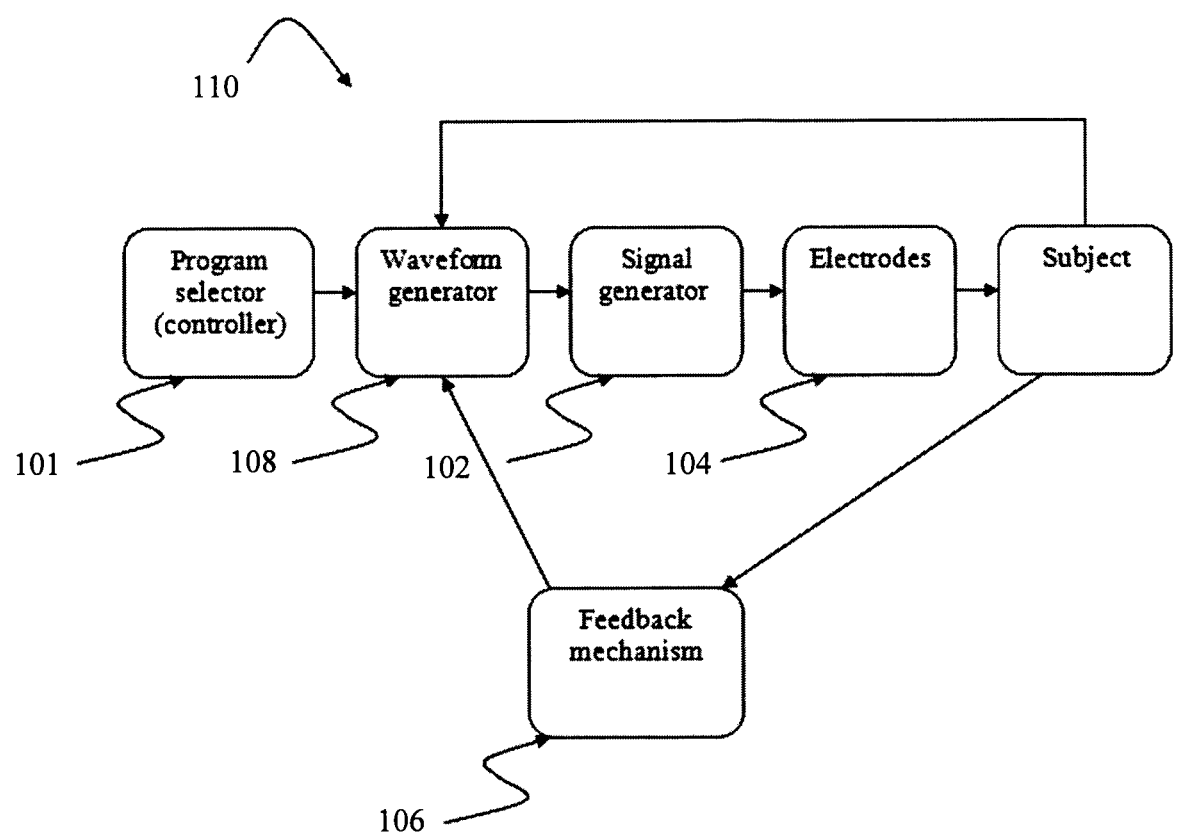
FIG. 2 is a schematic illustration of the device of the present invention.

Reference is now made to FIG. 2, which schematically illustrates the feedback mechanism of the present invention. As part of its operation, the RF generator of the present invention is configured to generate pulses of current to RF electrodes. This can be done, for example, after a program has been set by the controller. RF generator 108 sets the desired signal through a signal generator 102, which transmits the signal to RF electrodes 104. A feedback mechanism 106 assures the ability to improve the next treatment by updating and storing waveforms or waveform combinations achieving the highest scores on same or previous treatments.

According to different embodiment of the present invention, the treatment protocol comprises parameters selected from the group consisting of: power of each of the RF electrodes, length of pulse of each of the RF electrodes, frequency of each of the RF electrodes, the frequency of pulses of each of the RF electrodes, the structure of the pulses of each of the RF electrodes, and any combination thereof. The shape of the pulse may be one of the following: triangular, rectangular, ramp, sinusoidal, composite, sawtooth shape, and any combination thereof. The frequency of each of the RF electrodes ranges between about 1 Hz to about 100 MHz. The length of pulse of each of the RF electrodes ranges between about 1 micro seconds to about 1000 milliseconds.

It should be emphasized that it is postulated that the shape of the waveform, not only its electrical parameters, influence the results of the treatment procedure. Additionally, a synergistic effect by combining different basic waveforms may also be achieved by the treatment protocol. According to some embodiments, device 100 further comprises an input subsystem for determining the parameters of the treatment protocol.

According to some embodiments, substrate 20 is a thin substrate which is characterized by a thickness of between about 20 micrometer to about 25 cm. The substrate may be made of a non-conductive but thermally conductive material and/or an electrically insulating material.

According to different embodiments, substrate 20 may be made of a materials selected from the group consisting of: polyimide, polyester, silicone, plastic, polymeric fabric, polyurethane, textile, cloth, of wool, flax, cotton and any combination thereof.

According to some embodiments of the present invention, the parameters of the treatment protocol may be changeable during the treatment according to various circumstances. This various circumstances may be for example: an overheating of the skin, a preprogrammed change as part of the treatment protocol, an unexpected event, or any combination thereof.

According to some embodiments of the present invention, the input subsystem may be controllable by the patient himself According to other embodiments, the input subsystem may be controllable by the operator.

According to some embodiments of the present invention, the input subsystem is adapted to provide fine tuning of the parameters of the treatment protocol. For example, the fine-tuning is adapted to change the temperature generated by the RF electrodes in a range of ±2°.

According to some embodiments, device 100 may comprises a cooling unit adapted to cool the skin during the treatment procedure.

According to some embodiments, the device may comprise electronic components arranged in the substrate. The electronic components are selected from the group consisting of: resistors, capacitors, transistors, current regulators, and any combination thereof.

According to some embodiments, the substrate is adapted to conform to a non-planar treatment surface of the skin. For example, the substrate is adapted to be worn on the patient.

According to some embodiments, device 10 may comprise an adhesive adapted to secure the substrate from the first side to a portion of the skin, with the subtract conforming thereto.

According to some embodiments, the RF electrodes are adapted to heat a plurality of predetermined locations on the skin.

According to some embodiments, device 100 may comprise a pulsed electromagnetic field (PEMF) frequency generator for constantly providing electromagnetic pulses to the skin of the patient. Surprisingly, it was found that applying simultaneously different electrical signals leads to better esthetic results.

According to some embodiments, device 100 is adapted for simultaneously applying heat by the RF electrodes and PEMF to the skin of the patient; further wherein the simultaneous application of increases the results of the treatment such that this increase is greater than the sum of the increases when the treatment is performed by the RF electrodes and the PEMF not simultaneously. According to some embodiments, the electromagnetic pulse is a triangular shaped at frequency of 15 Hz, duration of about 5 milliseconds and intensity of 15 Gauss. According to other embodiments, the shape of the electromagnetic pulse may be selected from a group consisting of square wave, a sine wave, a triangular wave, sawtooth wave, ramp waves, spiked wave or any other mathematical combination.

By applying simultaneously at least two electrical signals by said PEMF, the device increases said skin beautification such that said increase is greater than the sum of said first signal increase and said second signal increase and said third signal increase.

According to another embodiment of the present invention, each of the above mentioned devices may additionally comprise a controller coupled to the electrical signal generator, adapted to enable selection of each said electrical signals applied to said region. According to another embodiment of the present invention, the selection is performed by patient.

According to another embodiment of the present invention the electrical treatment is provided only in safe treatment parameters. With respect to parameters that characterize the invention disclosed herein and the cosmetic treatment effected thereby, "unsafe" parameters are understood to be parameters that will cause tissue damage or excessive discomfort to the person undergoing treatment, e.g. overheating, transmitting energy to tissue layers below the skin, etc. According to one embodiment, the device of the present invention automatically prevents the parameters from reaching the unsafe zone and maintains the same within the safe zone.

According to one embodiment of the present invention, the device of the present invention may be applied for treatment of the skin of the face. The skin and muscles of the face are structured differently than other places on the body. One side of the facial muscles is connected to the bone and the other to the skin. As the muscle deteriorates through age the attached facial skin loses it elasticity. Loss of elasticity causes the skin to sag and wrinkle.

According to different embodiments of the present invention, the device is especially adapted to operate according to IEC selected from a group consisting of IEC 60601-2-35, IEC 60601-2-2, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

The modularity of the device is provided by ability to change the size of the substrate by adding and removing elements, such that a predetermined size of the substance is received.

According to certain embodiments of the present invention, the device of the present invention may be modular. This means that, for example, the size of the substrate may vary according to the parts and the elements it is constructed of. The size of the substrate may be changed by adding and removing elements, such that a predetermined size of the substance is received. The modularity of the device may be used for adaptation of the device to different parts of the body of the person. According to some embodiments, the device may be a "lego-like" device. According to this embodiment, each of the elements may have a connection sub-element (FIG. 1, 25) which is adapted to connect the element to its neighboring elements. According to other embodiments, the by using the modularity of the device, the dimensions of the device may change in each of its dimensions (i.e., 1D, 2D, 3D).

It is further within the scope of the present invention, wherein during treatment, in real time a feedback mechanism alter the treatment protocol/parameters so as to provide a safe treatment/better cosmetics/esthetic results.

It should also be appreciated that the above described description of methods and apparatus are to be interpreted as including apparatus for carrying out the methods, and methods of using the apparatus of any type as well known to a person or ordinary skill, and which need not be described in detail herein for enabling a person of ordinary skill to practice the invention.

It is within the scope of the present invention to provide the device as defined above, wherein said plurality of RF electrodes comprises N pairs of RF electrodes, each of said pairs in independent communication with RF generating means, said RF electrodes configured to transmit RF energy to said skin; further wherein said RF generator is adapted to generate N independent RF signals of predetermined waveforms, frequencies, amplitudes, and relative phases.

It is another object of the present invention to provide the device as defined above, additionally comprising control means for controlling the output of said RF generator, said control means in communication with said RF generator; and, an electrically insulating casing adapted to hold said RF electrodes such that said RF electrodes may be placed in simultaneous physical contact with said skin; wherein said N independent RF signals are phase shifted relative to one another.

It is another object of the present invention to provide the device as defined above, wherein the time-dependent amplitude $A_{t,m}$ of the mth of said N independent RF signals is given by the relationship $A_{t,m} = A_{0,m} \cdot F_m(\omega_m t + \varphi_m)$ where $A_{0,m}$ is a predetermined constant which greater than or equals to 1, $F_m$ is a predetermined periodic function of time, $\omega_m$ is the angular frequency of the mth RF signal, and $\varphi_m$ is a predetermined phase shift of the mth RF signal.

It is another object of the present invention to provide the device as defined above, wherein for each of said N independent RF signals, $$\varphi_m = \frac{\pi(m-1)k}{N},$$

where $0 \leq k \leq 1$ and $m = 1, 2, 3 \ldots N$; where N is the amount of said RF electrodes pairs.

It is another object of the present invention to provide the device as defined above, wherein $F_m$ is chosen from the group consisting of sine, cosine, tan, cotangents (cot), sawtooth wave, triangular wave, square wave, rectangular wave, trapezoidal wave, and any combination of the above.

Reference is now made to FIG. 3, which illustrates the above mentioned embodiment. FIG. 3 presents graphical representations of non-limiting examples of RF signals that may be applied to the electrode arrangement. In these graphs, the normalized amplitude of the signal is given as a function of ωt. In each graph, the curve corresponding to the signal transmitted to a particular pair of electrodes is labeled with the same letter as the corresponding pair of electrodes.

Figure 3A:
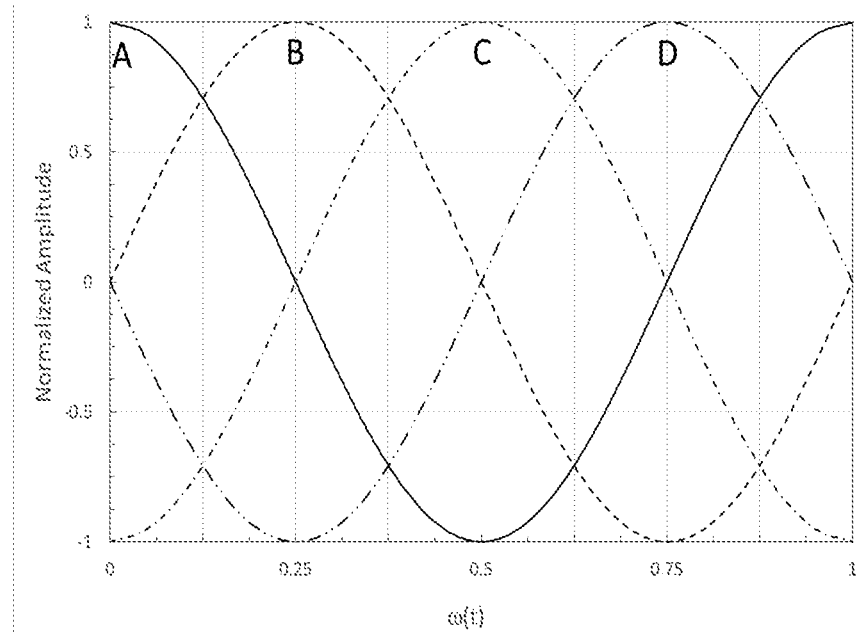
FIGS. 3a-3d illustrate a series of graphs illustrating the RF signal as a function of time for various embodiments of the invention.

FIG. 3A presents an embodiment in which N is 4, $F_m$ is a sine function, $$\varphi_m = \frac{\pi(m-1)k}{N}$$

where k=1 and N=4; and $A_{0,m}$ is 1.

Figure 3B:
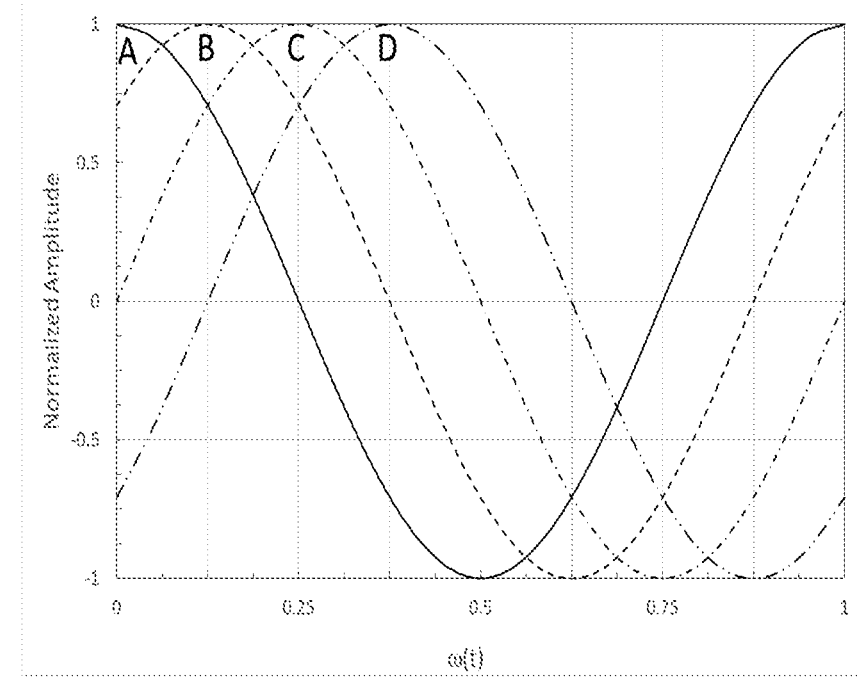

FIG. 3B presents an embodiment in which N is 4, $F_m$ is a sine function, $$\varphi_m = \frac{\pi(m-1)k}{N}$$

where k=1 and N=4, and $A_{0,m}$ is 1.

Figure 3C:
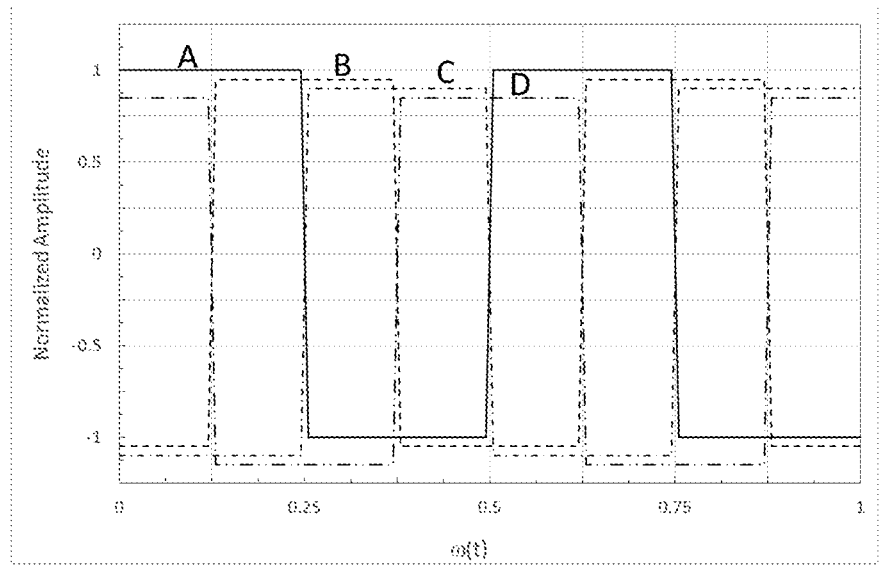

FIG. 3C presents an embodiment in which N is 4, $F_m$ is a square wave function, $\varphi_m$ $$\varphi_m = \frac{\pi(m-1)k}{N}$$

where k=1 and N=4; in this case, for clarity of presentation, two cycles are shown (i.e. the x-axis is actually 2 ωt), and the amplitudes of curves B, C, and D have been offset from 1. Thus, $A_{0,m}$ for A is 1; $A_{0,m}$ for B is 0.95, $A_{0,m}$ for C is 0.9; and, $A_{0,m}$ for D is 0.85.

Figure 3D:
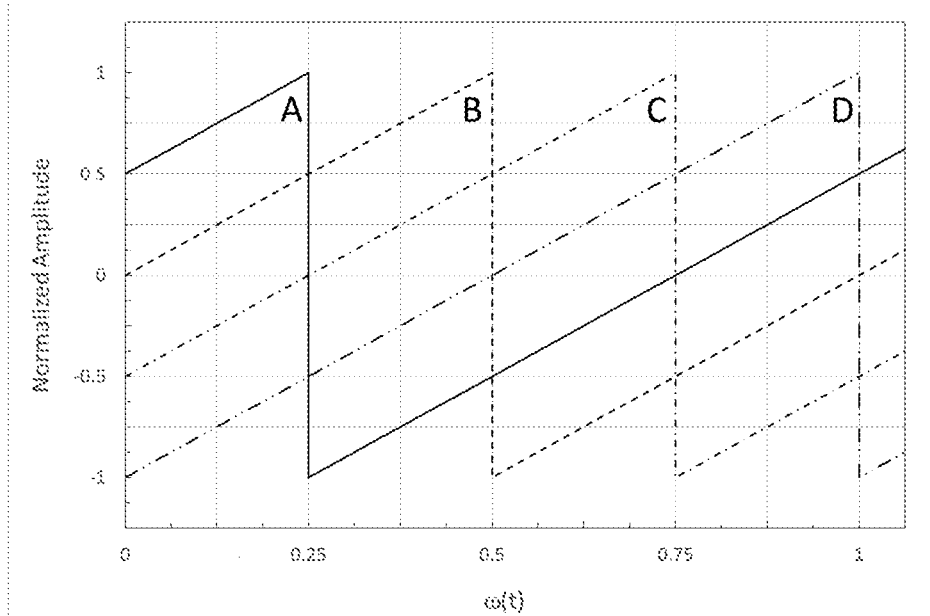

FIG. 3D presents an embodiment in which the waveform is a sawtooth function and $$\varphi_m = \frac{\pi(m-1)k}{N}$$

where k=1 and N=4, and $A_{0,m}$ is 1.

As mentioned above, it is within the scope of the present invention to provide the device as defined above, wherein said plurality of RF electrodes comprises N pairs of RF electrodes, each of said pairs in independent communication with RF generating means, said RF electrodes configured to transmit RF energy to said skin; further wherein said RF generator is adapted to generate N independent RF signals of predetermined waveforms, frequencies, amplitudes, and relative phases.

It is another object of the present invention to provide the device as defined above, additionally comprising control means for controlling the output of said RF generator, said control means in communication with said RF generator; and, an electrically insulating casing adapted to hold said RF electrodes such that said RF electrodes may be placed in simultaneous physical contact with said skin; wherein said N independent RF signals are phase shifted relative to one another.

It is another object of the present invention to provide the device as defined above, wherein the time-dependent amplitude $A_{t,m}$ of the mth of said N independent RF signals is given by the relationship $A_{t,m}=A_{0,m} \cdot F_m\ (\omega_m t+\varphi_m)$, where $A_{0,m}$ is a predetermined constant which greater than or equals to 1, $F_m$ is a predetermined periodic function of time, $\omega_m$ is the angular frequency of the mth RF signal, and $\omega_m$ is a predetermined phase shift of the mth RF signal.

It is another object of the present invention to provide the device as defined above, wherein for each of said N independent RF signals, $$\varphi_m = \frac{\pi(m-1)k}{N},$$

where 0≤k≤1 and m=1, 2, 3 . . . N; where N is the amount of said RF electrodes pairs.

It is another object of the present invention to provide the device as defined above, wherein $F_m$ is chosen from the group consisting of sine, cosine, tan, cotangents (cot), sawtooth wave, triangular wave, square wave, rectangular wave, trapezoidal wave, and any combination of the above.

It is another object of the present invention to provide the device as defined above, wherein each of said predetermined frequencies is between about 1 Hz and about 100 MHz.

It is another object of the present invention to provide the device as defined above, wherein said RF signals are transmitted in either a continues mode or in pulses.

It is another object of the present invention to provide the device as defined above, wherein, when the RF is applied in pulses, the length of said pulses is between about 0.01 micro-sec and about 1 ms.

It is another object of the present invention to provide the device as defined above, additionally comprising means adapted to apply Pulsed Electromagnetic Field Therapy (PEMF).

It is another object of the present invention to provide the device as defined above, wherein the length of said pulses is between about 0.1 and about 1000 ms.

It is another object of the present invention to provide the device as defined above, further comprising temperature measuring means adapted to measure the temperature of the surface of said skin.

It is another object of the present invention to provide the device as defined above, wherein said temperature measuring means comprises at least one sensor chosen from the group consisting of impedance meter adapted to measure impedance across at least one of said pairs of RF electrodes; thermal sensor; thermometer; and any combination thereof.

It is another object of the present invention to provide the device as defined above, wherein said temperature measuring means are either come into contact with the skin or not in contact with the skin.

It is another object of the present invention to provide the device as defined above, wherein said control means are programmed to regulate the amount of RF energy transmitted to said skin such that the temperature of said skin remains within a predetermined range.

It is another object of the present invention to provide the device as defined above, wherein said predetermined range is between ambient temperature and 50° C.

It is another object of the present invention to provide the device as defined above, wherein said electrodes are disposed about the distal end of said casing in a geometry chosen from the group consisting of linear; zigzag; on the perimeter of a shape chosen from substantially polygonal, circular, oval, or irregular; within the area of a shape chosen from substantially polygonal, circular, oval, or irregular; and any combination of the above.

It is another object of the present invention to provide the device as defined above, wherein the power transmitted by said RF electrodes and said RF generating means to said skin is between 1 W and 700 W.

It is another object of the present invention to provide the device as defined above, wherein said cosmetic improvement is chosen from the group consisting of skin rejuvenation, reduction of the number of wrinkles, reduction of the depth of wrinkles, reduction of cellulite, skin tightening, circumferential reduction, and any combination of the above.

It is another object of the present invention to provide the device as defined above, further comprising cooling means adapted to cool said skin.

It is another object of the present invention to provide the device as defined above, wherein said cooling means are chosen from the group consisting of a Peltier effect cooling device, irrigation with cool water, and means for blowing air across the skin.

It is another object of the present invention to provide the device as defined above, wherein said RF electrodes are further adapted to provide heat to said skin.

It is another object of the present invention to provide the device as defined above, further comprising a deep tissue diathermy device.

It is another object of the present invention to provide the device as defined above, wherein said deep tissue diathermy device is chosen from the group consisting of any devices emitting RF radiation and any other means adapted for producing electrical current absorbed by subcutaneous tissue.

It is another object of the present invention to provide the device as defined above, wherein said deep tissue diathermy device further comprises:
  i. at least one electrical output device adapted to generate RF electromagnetic energy; and,
  ii. at least two electrodes electrically coupled to said electrical output device and placed on said skin region, wherein all said electrodes are adapted to simultaneously apply said RF energy to said skin.

It is another object of the present invention to provide the device as defined above, wherein said deep tissue diathermy device further comprises:
  i. at least one electrical output device adapted to generate electrical current; and,
  ii. at least two electrodes electrically coupled to said electrical output device and placed on said skin region, wherein all of said electrodes are adapted to simultaneously apply said electrical current to said skin.

It is another object of the present invention to provide the device as defined above, wherein said deep tissue diathermy device is chosen from the group consisting of acoustic (e.g., ultrasonic) diathermy devices, optical diathermy devices, electromagnetic induction diathermy devices, devices for producing sound waves, ultrasonic diathermy devices, and devices for direct application of heat.

It is another object of the present invention to provide the device as defined above, wherein said deep tissue diathermy device is an optical device adapted to emit light in wavelengths absorbed by subcutaneous tissue such that said subcutaneous tissue is heated.

It is another object of the present invention to provide the device as defined above, wherein said deep tissue diathermy device is a device for producing sound waves adapted to emit sound waves of a frequency absorbed by the subcutaneous tissue such that said subcutaneous tissue is heated.

It is another object of the present invention to provide the device as defined above, wherein said control means are adapted to monitor physical tissue parameters and to change at least one of (a) the amount of heat applied and (b) the form of said RF in response to the values of said physical tissue parameters.

It is another object of the present invention to provide the device as defined above, wherein said control means further comprise:
  i. processing means adapted to store in a communicable database predetermined parameters defining safe and unsafe treatment parameters, said parameters chosen from the group consisting of time of said treatment, the temperature of said skin, frequency, power, energy applied by said RF generating means, depth to which said device operates, magnetic field intensity, tissue impedance, specific absorption rate, superficial muscle contractions and any combination thereof;
  ii. sensing means adapted to sense electromagnetic radiation and heat radiation parameters chosen from a group consisting of time of said treatment, temperature of said tissue, frequency, power, intensity of ultrasound irradiation, energy applied by said RF generating means, depth to which said device operates, magnetic field intensity, tissue impedance, specific absorption rate, superficial muscle contractions and any combination thereof; and,
  iii. regulating means adapted to stop the operation of said device if said parameters are determined to be unsafe.

It is another object of the present invention to provide the device as defined above, wherein said control means additionally comprise a feedback mechanism, adapted to change said RF signal according to predetermined medical needs, and comprising:
  i. sensing means adapted to monitor electrotherapy parameters related to the level of skin rejuvenation and viability;
  ii. processing means, adapted to determine the degree of esthetic improvement in at least one tissue parameter related to the level of skin rejuvenation and vitality; and,
  iii. regulating means adapted to stop the operation of said device when said degree of esthetic improvement reaches a predetermined value.

It is another object of the present invention to provide the device as defined above, wherein said electrotherapy parameters are chosen from the group consisting of dermal tensile forces, tissue impedance, muscle contraction forces, skin elasticity, and any combination thereof.

It is another object of the present invention to provide the device as defined above, wherein said at least one tissue parameter is chosen from the group consisting of dermal tensile forces, tissue impedance, muscle contraction forces, skin elasticity, and any combination thereof.

It is another object of the present invention to provide the device as defined above, wherein said sensing means are adapted to sense electrotherapy parameters are chosen from the group consisting of time of said treatment, temperature of said tissue, frequency, power, tissue impedance, superficial muscle contractions and any combination thereof.

It is another object of the present invention to provide the device as defined above, wherein said processing means are adapted to store in a communicable database predetermined parameters defining safe and unsafe treatment conditions.

It is another object of the present invention to provide the device as defined above, wherein said predetermined parameters are chosen from the group consisting of time of said treatment, temperature of said tissue, frequency, power, tissue impedance, superficial muscle contractions, and any combination thereof.

It is another object of the present invention to provide the device as defined above, additionally comprising means for massaging said skin.

It is another object of the present invention to provide the device as defined above, wherein at least one of said RF electrodes comprises a hypodermic syringe for penetrating into subcutaneous tissue.

It is another object of the present invention to provide the device as defined above, additionally comprising at least one acoustic transducer in communication with said substrate, adapted for producing ultrasonic waves.

It is another object of the present invention to provide the device as defined above, additionally comprising at least one first coil wrapped around at least a portion of said at least one acoustic transducer.

It is another object of the present invention to provide the device as defined above, wherein said at least one acoustic transducer is a piezoelectric transducer.

It is another object of the present invention to provide the device as defined above, additionally comprising a plurality of acoustic transducers, wherein a single coil is wrapped around all of said acoustic transducers.

It is another object of the present invention to provide the device as defined above, additionally comprising means for evacuating at least a portion of the skin so as to apply either pulses of suction or a constant vacuum.

It is another object of the present invention to provide the device as defined above, further comprising temperature measurement means and control means adapted to regulate at least one said RF electrical current, said time-varying current, and said alternating current such that the measured skin temperature does not go outside of predetermined limits.

It is another object of the present invention to provide the device as defined above, wherein said predetermined limits are ambient temperature and 45° C.

It is another object of the present invention to provide the device as defined above, wherein said predetermined limits are ambient temperature and 50° C.

It is another object of the present invention to provide the device as defined above, further comprising means for cooling the skin.

It is another object of the present invention to provide the device as defined above, wherein said means for cooling the skin is chosen from the group consisting of a Peltier effect cooling device, irrigation with cool water, and means for blowing air.

It is another object of the present invention to provide the device as defined above, additionally comprising at least one selected from a group consisting of light means, laser means, electrical energy generating means and any combination thereof embedded within said substrate.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for treating a skin of a patient, comprising:
   a. a substrate having a first side and a second side;
   b. a plurality of RF electrodes arranged in said substrate, said RF electrodes are configured to emit RF radiation from said first side to a surface of said skin;
   c. at least one RF generator configured to generate pulses of current to said RF electrodes; and,
   d. a control unit connected to said at least one RF generator, said control unit is configured to control operation of said RF electrodes;
   wherein said control unit is configured to control the operation of said RF electrodes according to a predetermined treatment protocol, such that the same activates or deactivates at least one of said RF electrodes at any predetermined time interval according to a predetermined pattern so as to achieve a particular therapeutic result; wherein said predetermined pattern is configured to mimic a treatment in which an applicator with RF electrodes is moved on the surface of said skin;
   wherein said device comprises a feedback mechanism connected to said control unit and configured to change parameters of said treatment protocol, according to predetermined parameters; said feedback mechanism configured to change said current to said RF electrodes according to predetermined medical needs, said feedback mechanism comprising:
   a. at least one sensor configured to sense at least one electrotherapy parameter selected from a group consisting of dermal tensile forces, tissue impedance, muscle contraction forces, skin elasticity, and any combination thereof;
   b. a processor, configured to generate a score of at least one analyzed tissue parameter according to a predetermined scale of treatment success; said at least one analyzed tissue parameter selected from a group consisting of: dermal tensile forces, tissue impedance, muscle contraction forces, skin elasticity, and any combination thereof-said change in said parameters of said treatment protocol and said change in said current based on said score; and,
   c. at least one regulator, configured to allow said treatment if said score is higher than a predetermined value and to stop said treatment if said score is lower than a predetermined value;
   said regulator configured to provide said treatment only in surroundings of an area in which said score is higher than a predetermined value
   wherein said processor is configured to store said score, and to update, based on said score, for at least one said treatment protocol, at least one selected from a waveform group consisting of a waveform and a waveform combination, said waveform group having achieved a highest score in at least one treatment.

2. The device according to claim 1, wherein at least one of the following is being held true (a) said substrate is substantially flexible; (b) said substrate is configured to be incorporated within an object selected from a group consisting of: a bed, a mattress, a chair, a treatment device placeable on said patient's skin, and a clothing element; (c) said treatment protocol is configured to activate or deactivate at any of said time intervals a substantially different set of RF electrodes; said set of electrodes comprising n RF electrodes, where n is greater than or equal to 1; and (d) the device comprises an adhesive configured to secure the substrate from the first side to a portion of the skin, with the substrate conforming thereto.

3. The device according to claim 1, further comprising temperature estimation mechanism for direct or indirect measurement of the skin heat distribution and temperature; wherein said temperature estimation mechanism comprises at least one sensor selected from a group consisting of: an impedance meter for measuring impedance across said RF electrodes; thermal sensor; light sensor, ultrasonic sensor, piezoelectric sensor, magnetic sensor, mechanical sensor, and any combination thereof.

4. The device according to claim 1, wherein at least one of the following is being held true (a) said device is modular, wherein the modularity of said device is provided by ability to change the size of said substrate by adding and removing elements, such that a predetermined size of said substance is received; (b) said treatment is a safe treatment, such that unexpected thermal injury to said skin is prevented; further wherein a temperature of said skin during said treatment is prevented from increasing beyond 45° C.; and (c) further comprising an input subsystem for manually determining the parameters of said treatment protocol; wherein said input subsystem is controllable by a person selected from a group consisting of: the patient himself, the operator, and any combination thereof; further wherein said input subsystem is configured to provide fine tuning of the parameters of said treatment protocol; said fine-tuning is configured to change the temperature generated by said RF electrodes in a range of ±2° C.

5. The device according to claim 1, further comprising a plurality of contact sensors in communication with said control unit, said sensors are configured to detect the areas on said substrate in which said substrate is proximal to said skin; further wherein said control unit is configured to activate or deactivate only RF electrodes in which said contact sensors detected proximity between said substrate and said skin; further wherein said plurality of contact sensors are selected from a group consisting of: thermal sensors, light sensors, ultrasonic sensors, piezoelectric sensors, magnetic sensors, mechanical sensors, pressure sensors, and any combination thereof; further wherein said contact sensors are either integrated with said RF electrodes; or, positioned between said RF electrodes.

6. The device according to claim 1, wherein said treatment protocol comprises parameters selected from a group consisting of: power deliverable by each of said RF electrodes, length of pulse deliverable by each of said RF electrodes, frequency RF deliverable by each of said RF electrodes, frequency of pulses deliverable by each of said RF electrodes, shape of said pulses deliverable by each of said RF electrodes, and any combination thereof; further wherein at least one of the following is being held true (a) said shape is selected from a group consisting of: triangular, rectangular, ramp, sinusoidal, composite, sawtooth shape, and any combination thereof; (b) said frequency of each of said RF electrodes ranges between 1 Hz and 100 MHz; (c) said length of pulse of each of said RF electrodes ranges between 1 microsecond and 1000 milliseconds; (d) said parameters of said treatment protocol are changeable during said treatment according to various circumstances; wherein said various circumstances are selected from: an overheating of said skin, a preprogrammed change as part of said treatment protocol, an unexpected event, and any combination thereof.

7. The device according to claim 1, wherein at least one of the following is being held true (a) in said substrate, said RF electrodes are arranged to form a shape selected from a group consisting of: a matrix, a line, at least one circle, a zig-zag, a polygon, an irregular shape, and any combination thereof; (b) said substrate is a thin substrate which is characterized by a thickness of between 20 μm and 25 cm; (c) said device further comprises a cooling unit configured to cool said skin; (d) said device further comprises electronic components arranged in said substrate, said electronic components are selected from a group consisting of: resistors, capacitors, transistors, current regulators, and any combination thereof; (e) said substrate is configured to conform to a non-planar treatment surface of said skin; (f) said substrate is configured to be worn on said patient; and any combination thereof.

8. The device according to claim 1, further comprising a pulsed electromagnetic field (PEMF) frequency generator for constantly providing electromagnetic pulses to said skin of said patient; at least one of the following being held true: (a) said device is configured for simultaneously applying heat by said RF electrodes and PEMF to said skin of said patient; (b) said electromagnetic pulse is square shaped at a frequency of 15 Hz, duration of 5 milliseconds and intensity of 15 Gauss; (c) the shape of said electromagnetic pulse is selected from a group consisting of a square wave, a sine wave, a triangular wave, a sawtooth wave, a ramp wave, a spiked wave and any combination thereof.

9. The device according to claim 1, wherein said plurality of RF electrodes comprises N pairs of RF electrodes, each of said pairs in independent communication with said RF generator, said RF electrodes configured to transmit RF energy to said skin; further wherein said RF generator is configured to generate N independent RF signals of predetermined waveforms, frequencies, amplitudes, and relative phases; and, an electrically insulating casing configured to hold said RF electrodes such that said RF electrodes may be placed in simultaneous physical contact with said skin; wherein said N independent RF signals are phase shifted relative to one another.

10. The device according to claim 9, wherein a time-dependent amplitude $A_{t,m}$ of the mth of said N independent RF signals is given by the relationship $A_{t,m}=A_{0,m} \cdot F_m(\omega_m t + \varphi_m)$, where $A_{0,m}$ is a predetermined constant greater than or equal to 1, $F_m$ is a predetermined periodic function of time, $\omega_m$ is the angular frequency of the mth RF signal, and $\varphi_m$ is a predetermined phase shift of the mth RF signal; wherein for each of said N independent RF signals, $$\varphi_m = \frac{\pi(m-1)k}{N},$$

where $0 \leq k \leq 1$ and m=1, 2, 3 ... N; where N is the amount of said RF electrodes pairs; further wherein $F_m$ is chosen from a group consisting of sine, cosine, tangent, cotangent, sawtooth wave, triangular wave, square wave, rectangular wave, trapezoidal wave, and any combination of the above.

11. The device according to claim 9, wherein at least one of the following is being held true (a) each of said predetermined frequencies is between 1 Hz and 100 MHz; (b) said RF signals are transmitted in either a continuous mode or in pulses; wherein, when said RF is applied in pulses, the length of said pulses is between 0.01 μs and 1 ms; (c) said device is configured to apply Pulsed Electromagnetic Field Therapy (PEMF); a length of said pulses is between 0.1 ms and 1000 ms; (d) power transmitted by said RF electrodes and said RF generator to said skin is between 1 W and 700 W; (e) said RF electrodes are further configured to provide heat to said skin; (f) said device further comprises at least one temperature sensor configured to measure temperature of said surface of said skin; said at least one temperature sensor selected from a group consisting of: impedance meter configured to measure impedance across at least one of said pairs of RF electrodes; thermal sensor; and any combination thereof; wherein said at least one temperature sensor either comes into contact with said skin or does not come in contact with said skin; (g) further comprising at least one cooling unit configured to cool said skin; said at least one cooling unit selected from a group consisting of: a Peltier effect cooling device, irrigation with cool water, and a device for blowing air across said skin.

12. The device according to claim 9, wherein said control unit is configured to monitor physical tissue parameters and to change at least one of (a) the amount of heat applied and (b) the form of said RF in response to the values of said physical tissue parameters.

13. The device according to claim 12, wherein at least one of the following is being held true (a) said electrotherapy parameters are chosen from a group consisting of dermal tensile forces, tissue impedance, muscle contraction forces, skin elasticity, and any combination thereof; (b) said at least one tissue parameter is chosen from a group consisting of dermal tensile forces, tissue impedance, muscle contraction forces, skin elasticity, and any combination thereof; (c) said sensor is configured to sense at least one electrotherapy parameter selected from a group consisting of: time of said treatment, temperature of said tissue, frequency, power, tissue impedance, superficial muscle contractions and any combination thereof; and (d) said processor is configured to store in a communicable database at least one predetermined parameter defining safe and unsafe treatment conditions; said at least one predetermined parameter selected from a group consisting of: time of said treatment, temperature of said tissue, frequency, power, tissue impedance, superficial muscle contractions, and any combination thereof.

14. The device according to claim 1, wherein at least one of the following is true (a) said device additionally comprises a suction unit for evacuating adjacent to at least a portion of said skin so as to apply either pulses of suction or a constant vacuum to said skin; and (b) said device further comprises at least one temperature sensor and a control unit configured to regulate at least one said current to said RF electrodes, thereby keeping measured skin temperature within predetermined limits.

15. The device according to claim 1, wherein said substrate is made of an electrically insulating material.

16. The device according to claim 1, wherein said substrate is made of a material selected from a group consisting of: polyimide, polyester, silicone, plastic, polymeric fabric, polyurethane, textile, cloth, wool, flax, cotton and any combination thereof.

17. A method for treating a skin of a patient, comprising steps of:
- a. providing a device for treating a skin of a patient, comprising: (i) a substrate having a first side and a second side; (ii) a plurality of RF electrodes arranged in said substrate, said RF electrodes are configured to emit RF radiation from said first side to a surface of said skin; (iii) at least one RF generator configured to generate pulses of current to said RF electrodes; and, (iv) a control unit connected to said at least one RF generator, said control unit is configured to control the operation of said RF electrodes;
- b. at least partially contacting said substrate to said skin of said patient or bringing said substrate adjacent to said skin of said patient;
- c. activating at least one of said RF electrodes at any predetermined time interval according to a predetermined pattern; and,
- d. controlling said RF electrodes according to a predetermined treatment protocol thereby activating or deactivating at least one of said RF electrodes at any predetermined time interval according to a predetermined pattern and achieving a particular therapeutic result; wherein said predetermined pattern is configured to mimic a treatment in which an applicator with RF electrodes is moved on the surface of said skin;

wherein said method additionally comprises steps of:
- a. providing said device with a feedback mechanism connected to said control unit; said feedback mechanism comprising:
  - i. at least one sensor configured to sense at least one electrotherapy parameter selected from a group consisting of dermal tensile forces, tissue impedance, muscle contraction forces, skin elasticity, and any combination thereof;
  - ii. a processor, configured to generate a score of at least one analyzed tissue parameter according to a predetermined scale of treatment success; said at least one analyzed tissue parameter selected from a group consisting of: dermal tensile forces, tissue impedance, muscle contraction forces, skin elasticity, and any combination thereof, said change in said parameters of said treatment protocol and said change in said current based on said score; and,
  - iii. at least one regulator, configured to allow said treatment if said score is higher than a predetermined value and to stop said treatment if said score is lower than a predetermined value;
- b. changing parameters of said treatment protocol, according to predetermined parameters; and
- c. changing said current to said RF electrodes according to predetermined medical needs;

wherein said regulator provides said treatment only in surroundings of an area in which said score is higher than a predetermined value wherein said processor additionally comprises steps of (a) storing said score, and (b) updating, based on said score, for at least one said treatment protocol, at least one selected from a waveform group consisting of a waveform and a waveform combination, said waveform group having achieved a highest score in at least one treatment.

18. The method according to claim 17, wherein said step (b) of contacting said substrate further comprising a step of locating said patient on an object selected from a group consisting of: a bed, a mattress, a chair, a hand-held treatment device, and a clothing element.

19. The method according to claim 17, further comprising at least one step of (a) activating at any of said time intervals a set of RF electrodes according to said treatment protocol wherein said set of RF electrodes comprises n RF electrodes, where n is greater than or equal to 1; (b) directly and indirectly measuring the heat distribution and temperature of said skin via a temperature estimation mechanism; wherein said temperature estimation mechanism comprises at least one sensor selected from a group consisting of: an impedance meter for measuring impedance across said RF electrodes; thermal sensor; light sensor, ultrasonic sensor, piezoelectric sensor, magnetic sensor, mechanical sensor, and any combination thereof.

20. The method according to claim 17, further comprising a step of detecting the areas on said substrate in which said substrate is proximal to said skin via a plurality of contact sensors in communication with said control unit; wherein said plurality of contact sensors are selected from a group consisting of: thermal sensors, light sensors, ultrasonic sensors, piezoelectric sensors, magnetic sensors, mechanical sensors, pressure sensors, and any combination thereof.

21. The method according to claim 20, wherein said contact sensors are either integrated with said RF electrodes or positioned between said RF electrodes.

22. The method according to claim 17, further comprising a step of preventing the temperate of said skin to increase beyond 45° C. during said treatment; wherein said treatment is a safe treatment, such that unexpected thermal injury to said skin is prevented.

23. The method according to claim 17, wherein said treatment protocol comprises parameters selected from a group consisting of: power deliverable by each of said RF electrodes, length of pulse deliverable by each of said RF electrodes, frequency of RF deliverable by each of said RF electrodes, frequency of pulses deliverable by each of said RF electrodes, shape of said pulses deliverable by each of said RF electrodes, and any combination thereof.

24. The method according to claim 23, wherein at least one of the following is being held true (a) said shape is selected from a group consisting of: triangular, rectangular, ramp, sinusoidal, composite, sawtooth, and any combination thereof; (b) said frequency of each of said RF electrodes ranges between 1 Hz and 100 MHz; (c) said length of pulse of each of said RF electrodes ranges between 1 microsecond and 1000 milliseconds.

25. The method according to claim 17, further comprising a step of manually determining the parameters of said treatment protocol via an input subsystem; wherein said input subsystem is controllable by a person selected from a group consisting of: the patient himself, the operator, and any combination thereof; wherein said input subsystem is configured to provide fine tuning of the parameters of said treatment protocol; said fine-tuning is configured to change the temperature generated by said RF electrodes in a range of ±2° C.

26. The method according to claim 17, wherein, in said substrate, said RF electrodes are arranged to form a shape selected from a group consisting of: a matrix, a line, at least one circle, a zig-zag, a polygon, an irregular shape, and any combination thereof.

27. The method according to claim 17, wherein at least one of the following is being held true (a) said substrate is made of a non-conductive but thermally conductive material; (b) said substrate is made of an electrically insulating material; (c) said substrate is made of a material selected from a group consisting of: polyimide, polyester, silicone, plastic, polymeric fabric, polyurethane, textile, cloth, wool, flax, cotton and any combination thereof; (d) said device further comprises a cooling unit configured to cool said skin; (e) said device further comprises electronic components arranged in said substrate, said electronic components selected from a group consisting of: resistors, capacitors, transistors, current regulators, and any combination thereof; (f) said substrate is configured to conform to a non-planar treatment surface of said skin; and (g) said substrate is configured to be worn on said patient.

28. The method according to claim 17, further comprising a step of providing said device with an adhesive which is configured to secure said substrate from said first side to a portion of said skin, with said substrate conforming thereto.

29. The method according to claim 17, further comprising a step of providing said device with a pulsed electromagnetic field (PEMF) frequency generator for constantly providing electromagnetic pulses to said skin of said patient; wherein said device is configured for simultaneously applying heat by said RF electrodes and PEMF to said skin of said patient; further wherein said simultaneous application of said pulses and said heat synergistically increases results of said treatment such that a result of treatment with said pulses and said heat applied simultaneously is greater than the sum of results from a treatment with said RF electrodes and a treatment with said PEMF applied non-simultaneously.

30. The method according to claim 29, wherein at least one of the following is being held true (a) said electromagnetic pulse is square shaped at a frequency of 15 Hz, duration of 5 milliseconds and intensity of 15 Gauss; and (b) the shape of said electromagnetic pulse is selected from a group consisting of a square wave, a sine wave, a triangular wave, a sawtooth wave, a ramp wave, a spiked wave and any other combination thereof.

31. The method according to claim 17, wherein said treatment is selected from a group consisting of: skin rejuvenation, smoothing wrinkles, skin tightening circumferential reduction, treatment of cellulite, and any combination thereof.

* * * * *